United States Patent [19]

Ponto

[11] Patent Number: Plant 7,403

[45] Date of Patent: Dec. 25, 1990

[54] *RAPHIOLEPIS INDICA* CV. PONTO'S PINK CLARA

[75] Inventor: William H. Ponto, Vista, Calif.

[73] Assignee: Ponto Nursery, Inc., Vista, Calif.

[21] Appl. No.: 339,651

[22] Filed: Apr. 18, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—Baker, Maxham, Jester & Meador

[57] ABSTRACT

A new and distinct selection of *Raphiolepis indica* (popularly known as Indian Hawthorn) which herein is referred to as *Raphiolepis indica* cultivar Ponto's Pink Clara. *Raphiolepis indica* cv. Ponto's Pink Clara differs from its parent plant by possessing a pink flower rather than white, and the leaves are more leathery and deeper in color.

2 Drawing Sheets

DISCOVERY

This invention relates to a new and distinct selection of *Raphiolepis indica,* a member of the rose family, Rosaceae and commonly known as Indian Hawthorn. *Raphiolepis indica* cv. Ponto's Pink Clara, the new variety, originated as a selected seedling from *Raphiolepis indica* "Clara" at Ponto Nursery, Inc., 2545 Ramona Drive, Vista, Calif., in the spring of 1982. The plant to date is known to exist only within the boundaries of Ponto Nursery and Flynn Rainbow Nursery, and has not been described in any publication.

The distinctive plant was selected out, allowed to develop and then asexually reproduced by cuttings and grafting for evaluation. Each of the progeny exhibit identical characteristics to the original selected prototype, establishing this variety as stable and true to type when produced by asexual means.

REPRODUCTION

This new selection has been strictly asexually reproduced by cuttings and grafting at Ponto Nursery and Flynn Rainbow Nursery. Sexual reproduction such as seed propagation would result in loss of selected attributes. Therefore sexual reproduction is prohibited and propagation is restricted to asexual reproduction by vegetative cuttings or grafts.

BRIEF DESCRIPTION OF THE PHOTOGRAPHS

The accompanying photographs show a typical specimen of the plant according to this invention in full color, demonstrating the unique and distinctive coloration of the flowers, the color rendition being as nearly true as it is possible to obtain by conventional procedures, in which:

FIG. 1 shows the complete plant of the new variety in a seven-gallon container at seven years of age from a cutting;

FIG. 2 is a close-up view displaying the flower and leaf colors;

FIG. 3 is a close-up view of a portion of the plant of FIG. 1 showing the color of the flowers and their relationship to the foliage; and FIG. 4 displays a close-up view of a spray of branches of the plant of this invention and several individual flowers.

CHARACTERISTICS

This new plant selection exhibits several of the desirable characteristics of the parent plant, such as its compact, mounding growth and free branching habit. Note from FIG. 1 the dense mounding habit with no pruning being necessary. *Raphiolepis indica* cv. Ponto's Pink Clara, as shown in FIGS. 2 and 3, displays massing clear pink flowers covering all foliage, whereas the parent plant has white flowers. Further, the foliage is thicker and deeper green in color than the parent plant, setting it aside as unique from the common species. The plant at seven years of age is approximately two and one-half feet high and about three feet across or in diameter.

Overall appearance of this new variety is a healthy, robust deep green mounding plant which freely branches from terminal clusters. The foliage is composed of obovate to oblong leaves which are slightly convex at the margin. Upon emergence they are coppery to bronze, this color being enhanced by cooler temperatures, darkening into a deep, dark, leathery green. At onset of bloom, typically in February, the plant is transformed into a mound of clear pink by the thousands of small flowers borne in clusters which profusely coat the plant. Flowers fade by late spring, normally around the end of May, and are replaced by occasional berries in June, which start light to medium green and then turn purple with the onset of winter. The fruit size is about 5/16 inch (7.94 mm) in diameter.

As can best be clearly seen from FIGS. 2 and 4, the flowers are a clear rosy pink which distinguish from the white flowers of the parent plant.

Disease and insect resistance: No disease or insect problems have occurred requiring other than normal nursery spraying practices and sanitary work methods common to all Raphiolepis.

With respect to climatic range, this new variety has withstood temperatures ranging from 28°-100° F. without any harmful effects. The plant species this selection is derived from is hardy in zone 8, Hortus III, where low temperatures range from 10°-20° F.

DESCRIPTION

This following is a detailed description of the new *Raphiolepis india* cv. Ponto's Pink Clara, the color terminology being from the Munsell Color System chart.

Plant:

*Overall size and growth habits.*—Evergreen, dense and mounding at seven years of age. Plant is approximately two and one half feet (0.76 m) high and three feet (0.91 m) wide at that age. Ultimate height is unknown but no plant of this variety has surpassed one meter in height or width. Compact, freely branching from apical parts of the branches lending to its low, dense mounding shape.

*Difference from parent raphiolepis indica Clara.*—Flowers pink instead of white and foliage more leathery and deeper in color.

Foliage:

*Length.*—Mature leaves are approximately three inches (7.6 cm) in length and 1¼ inch (3.2 cm) in width. They are alternate, simple, petiolate leaves which are evergreen and ascending. They are obovate to oblong with a narrowly cuneate base and broadly acute apex. An occasional truncate apex is noticed. The margins are serrate on the upper half only, with occasional convexing noticed on mature leaves. The petioles are 0.47 to 0.51 inch (1.2–1.3 cm) in length. Internode length varies from 0.59 inch down to 0.08 inch (1.5 cm down to 2 mm). Surface is glabrous.

*Color.*—Upper surface is a deep forest green, most closely related to color number 9GY 3.8/4. Under side is a more yellow/green, most closely related to color number 5GY 4.7/4.

*Texture.*—Medium to coarse.

Inflorescence: Borne in a basely branching panicle. They are perfect, complete, epigynous and regular with floral parts in fives. There are occasionally rudimentary bracts on the panicle. The pedicels measure from 0.12 to 0.35 inch (3 mm to 9 mm) in length, while the peduncle measures from 0.47 to 0.98 inch (12 mm to 25 mm) in length. The corolla is polypetalous, composed of five pink petals.

*Petal size.*—Each petal is approximately ½ inch (1.3 cm) in length and ⅓ inch (0.9 cm) in width.

*Petal shape.*—Oblanceolate with a rounded tip.

*Flower size.*—Overall corolla measures approximately 1¼ inch (3.2 cm) in width when fully open.

*Flower color.*—Clear, light rosy pink, most closely matches color number 4R 7.5/4. The calyx is composed of five sepals which are from 0.16 to 0.24 inch (4 to 6 mm) in length, narrowly acute. Sepals are a pale green, most closely matching color number 6GY 7/4, with a burgundy border, most closely matching color number 9RP 4.4/8. The filaments are white, darkening to a reddish pink with maturity.

*Fragrance.*—Light and insignificant.

I claim:

1. A new, distinct and different selection of *Raphiolepis indica* as substantially shown and described herein, that is characterized by green and leathery foliage, growth habits dense and mounding, and covered with single clear pink flowers.

* * * * *

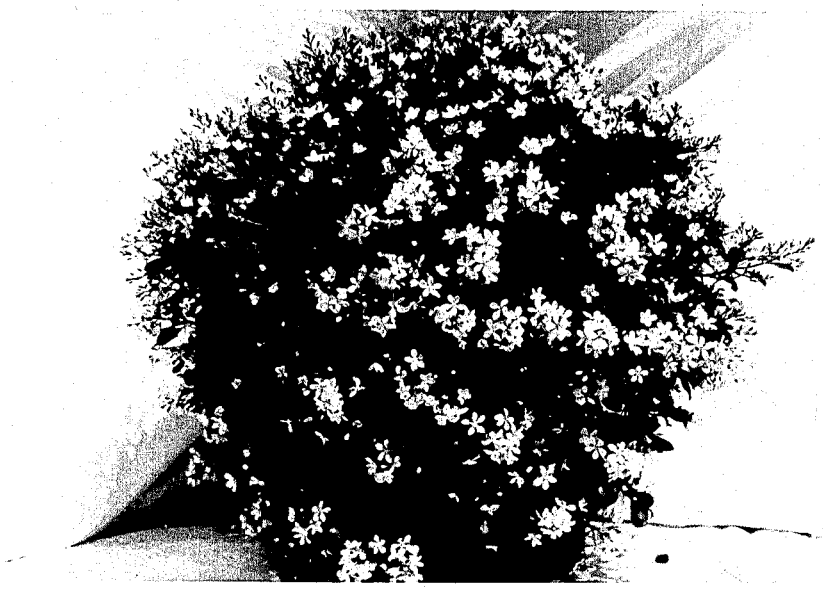
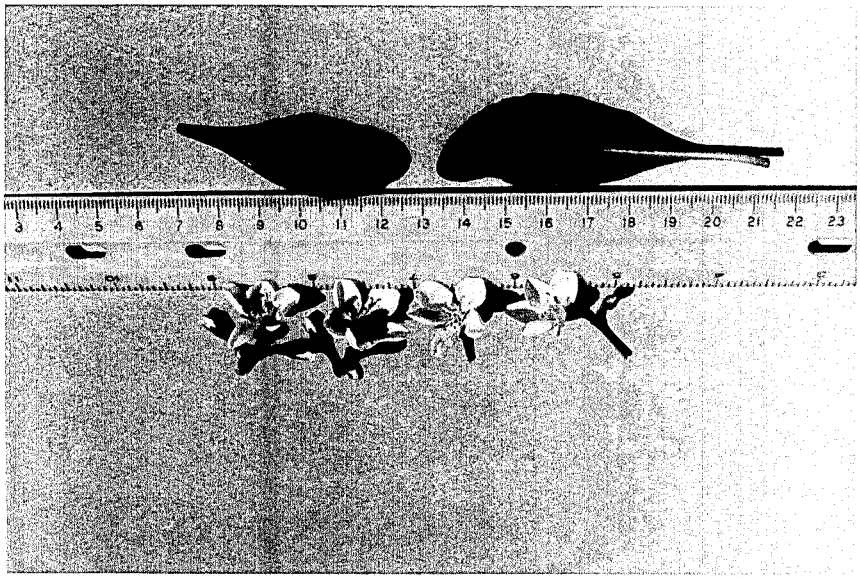
FIG. 2

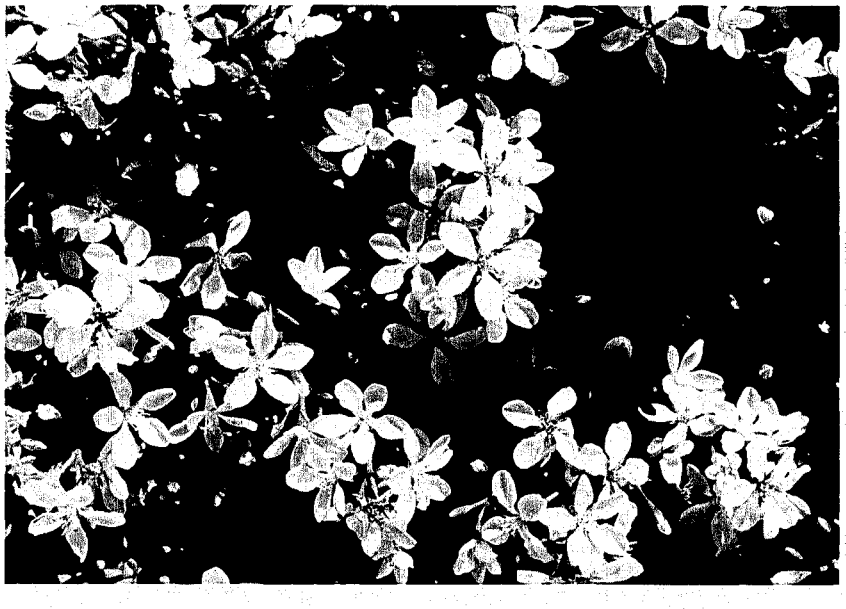
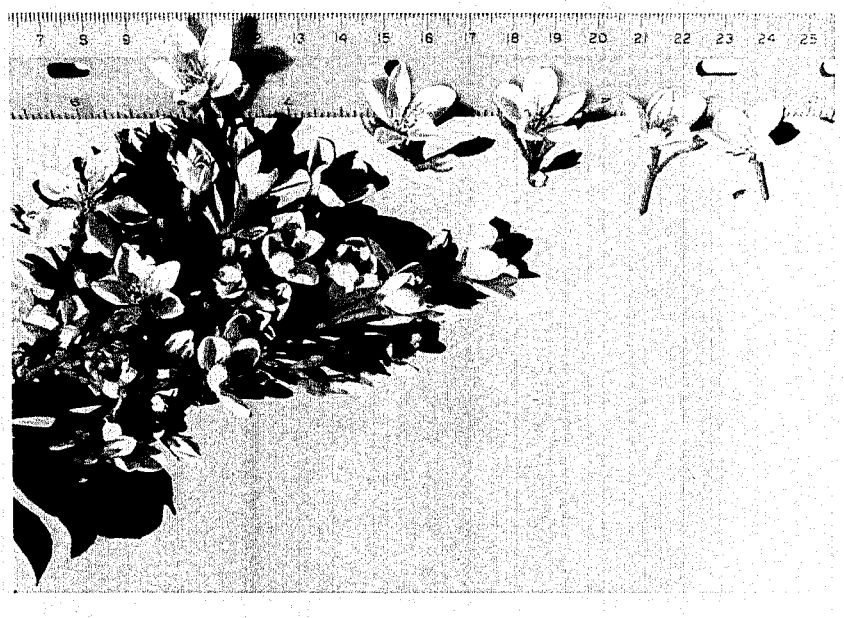
FIG. 4